United States Patent
Strong

[19]

[11] Patent Number: 6,083,152
[45] Date of Patent: Jul. 4, 2000

[54] ENDOSCOPIC INSERTION TUBE

[75] Inventor: James G. Strong, Skaneateles, N.Y.

[73] Assignee: Welch Allyn, Inc., Skaneateles Falls, N.Y.

[21] Appl. No.: 09/228,577

[22] Filed: Jan. 11, 1999

[51] Int. Cl.[7] ........................................... A61B 1/00
[52] U.S. Cl. .................. 600/139; 600/121; 600/140; 600/144
[58] Field of Search ................... 600/121, 122, 600/123, 124, 125, 139, 140, 143, 144, 151; 604/526, 527; 138/125, 141

[56] References Cited

U.S. PATENT DOCUMENTS

| | | |
|---|---|---|
| 3,670,721 | 6/1972 | Fukami et al. . |
| 3,960,143 | 6/1976 | Terada . |
| 4,327,711 | 5/1982 | Takagi ..................................... 600/139 |
| 4,347,837 | 9/1982 | Hosono ................... 600/139 |
| 4,753,222 | 6/1988 | Morishita . |
| 4,805,595 | 2/1989 | Kanbara ................................. 600/140 |
| 4,899,787 | 2/1990 | Ouchi et al. ............................ 600/131 |
| 5,058,568 | 10/1991 | Irion et al. ............................... 138/134 |
| 5,275,152 | 1/1994 | Krauter et al. ........................... 600/129 |
| 5,386,816 | 2/1995 | Inoue et al. .............................. 600/121 |
| 5,429,118 | 7/1995 | Cole et al. .............................. 600/121 |
| 5,465,710 | 11/1995 | Miyagi et al. .......................... 600/139 |
| 5,685,825 | 11/1997 | Takase et al. ........................... 600/140 |
| 5,746,696 | 5/1998 | Kondo .................... 600/139 |
| 5,873,866 | 2/1999 | Kondo et al. ........................... 604/526 |
| 5,876,331 | 3/1999 | Wu et al. ................................. 600/139 |
| 5,885,207 | 3/1999 | Iwasaka ................................. 600/139 |
| 5,885,209 | 3/1999 | Green ..................................... 600/153 |
| 5,938,587 | 8/1999 | Tatlor et al. ............................ 600/139 |
| 5,998,019 | 12/1999 | Rosenbaum et al. ................... 428/345 |

*Primary Examiner*—Linda C. M. Dvorak
*Assistant Examiner*—Brad C. Blaise
*Attorney, Agent, or Firm*—Wall Marjama Bilinski & Burr

[57] ABSTRACT

An endoscopic insertion tube includes a helically wound spiral tube and a net-like braid disposed in overlaying relation. A polymeric adhesive layer is applied over the length of the spiral tube and the outer peripheral surface of the braid. A pre-expanded hollow tubular sheath member is placed over the adhesive layer and is shrunk thereupon using heat to cross-link with the polymeric adhesive layer. The sheath includes a preferably multi-layer structure including at least an inner and an outer layer which can be co-extruded or applied to the assembly in separate sections. According to a preferred embodiment, the outer layer is a clear high-polymer material that allows printing applied to the exterior of the upper layer to be protected.

27 Claims, 3 Drawing Sheets

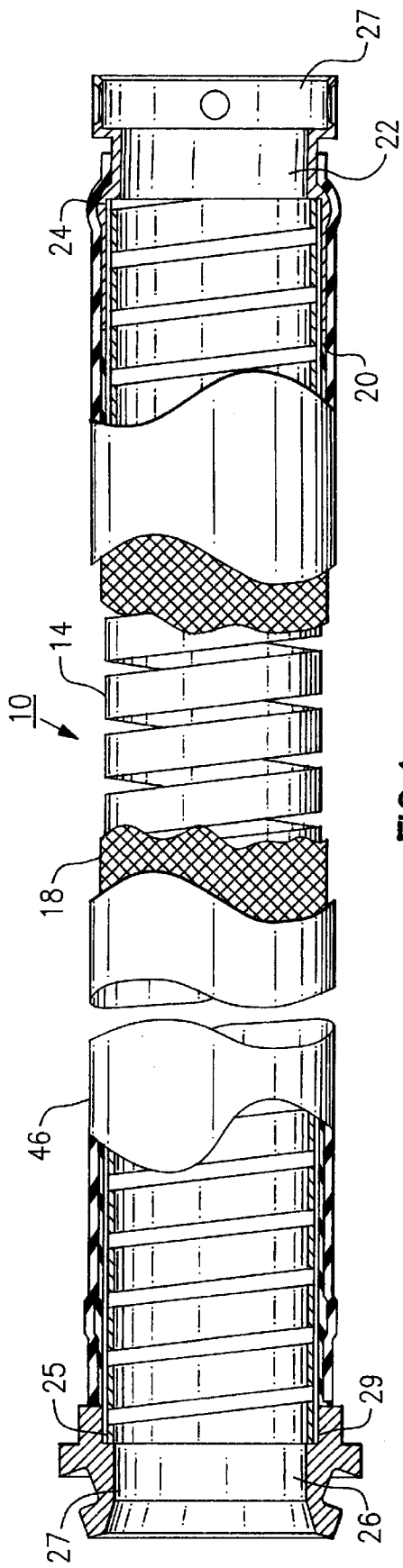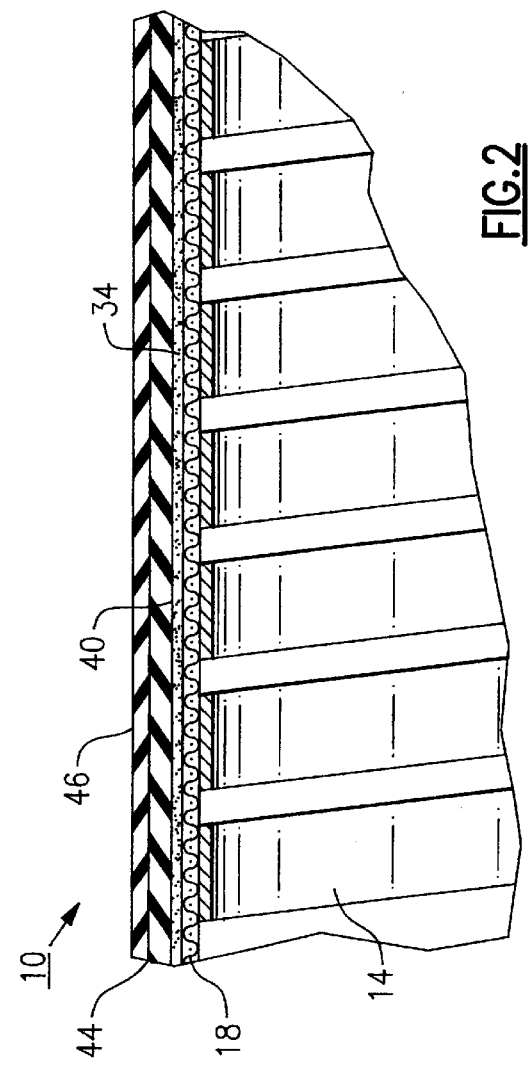

ENDOSCOPIC INSERTION TUBE

FIELD OF THE INVENTION

The invention relates to medical diagnostic instruments, and in particular to an endoscopic insertion tube and a related method for manufacturing the same.

BACKGROUND OF THE INVENTION

An endoscope is used to inspect body cavities, such as the colon, intestines, esophagus, etc. An elongate distal tubular insertion section of an instrument body carrying an imaging optical system and an illumination optical system. The insertion portion is inserted into and traverses through the body cavity to a target of particular interest. For the sake of ease and to reduce pain to the patient, the insertion portion should be as flexible as possible and allow control by the remote user, while still allowing illumination to be carried to the tip of the insertion portion and allowing image data to be transmitted therefrom. In addition, the tubular insertion portion must be made from a biocompatible material.

A prior art insertion tube is known and described in U.S. Pat. No. 3,670,721, issued to Fukami et al. In the instant reference, an insertion tube includes a thin metal section wound into a spiral tubular configuration and a net-like braid which is placed in overlaying relationship onto the length of the spiral tube. A molten layer of a synthetic resin or synthetic rubber is embedded into the braid, and subsequent molten layers can be added to existing layers to improve the handling characteristics of the tube. The described tube provides a reasonable amount of flexibility, but the molten layer is caused to penetrate into the braid, thereby degrading the overall elasticity of the tube.

In U.S. Pat. No. 4,753,222, to Morishita, an insertion tube is described, also having a similar spiral tube and a net-like braid placed in overlaying relation. According to this patent, an inner or intermediate tubular member made from a high-polymer material is then force-fitted over the outer periphery of the braid and a second or outer tubular member is formed by applying a molten high-polymer material onto the outer surface of the inner tubular member via a molding process or a die assembly process. The intermediate tubular member isolates the braid and spiral tube from the molten polymer material and therefore prevents deterioration of the restoration force of the braid and spiral tube.

While this tube provides additional advantages, it would appear that the instant tube, and particularly the desired force or interference fit of the intermediate layer relative to the braid and the spiral tube, is difficult to manufacture.

Another problem relates to the range markings found commonly on endoscopic insertion tubes. The markings are printed or otherwise applied to the outer surface of the tube and provide a guide as to the depth of penetration of the tube into the body cavity of interest. Because the outer surface of the tube must be biocompatible, it has been difficult to preserve the markings during the life of the insertion tube. Consequently, tubes must often be replaced before the useful life of the tube itself due to premature fading of the markings.

SUMMARY OF THE INVENTION

A primary object of the present invention is therefore to improve the state of the art of endoscopic instruments.

A further primary object of the present invention is to provide an improved and flexible insertion tube and method of manufacturing an insertion tube for an endoscope, such as a colonoscope, gastroscope, sigmoidoscope or other suitable instrument.

Therefore, and according to a preferred aspect of the present invention, there is provided a endoscopic insertion tube for insertion into a body cavity, said tube comprising:
  a helically wound spiral tube;
  a net-like braid placed over the length of said helically wound spiral tube in over laying relation;
  a polymeric adhesive layer coating the outer periphery of said braid; and
  a sheath covering said polymeric adhesive layer, said sheath comprising a multi layer structure including at least two layers, an inner layer fitted over the adhesive layer and an outer layer disposed over the outer peripheral surface of said inner layer, said inner layer and said outer layer each being made from a high-polymer material cross-linked together and in which said inner layer is cross-linked to said polymeric adhesive layer.

Preferably, each of the tubular sections of the sheath are fitted in a pre-expanded condition, wherein heat allows each tubular section to be shrunk onto the tube assembly, the heat being sufficient to first cross-link the inner layer with the adhesive layer and as well as the outer and inner layers.

The inner layer according to one embodiment can include multiple tubular sections composed of polymeric materials having different hardnesses, the tubular sections each being fitted onto the adhesive layer with the abutting edges of the tubular sections being fused to each other by heating and to bond the sheath to the braid.

In another embodiment, the inner layer includes printing on an outer peripheral surface and the outer sheath layer consists of a clear polymeric material which protects the printing and therefore increases the service life of the tube.

In yet another embodiment, the sheath is formed in a co-extrusion process defined by inner and outer layers which are cross-linked to one another. The sheath is then preferably fitted over the adhesive layer in a pre-expanded condition and is heated to allow the inner layer to cross-link with the adhesive layer and to allow shrinking to conform the tubular sheath to the tube assembly.

According to another preferred aspect of the present invention, there is described a process for manufacturing a flexible endoscopic insertion tube, the method comprising the steps of:
  placing a net-like braid over the length of a helical metal inner coil member in overlaying fashion;
  applying a polymeric adhesive layer onto the outer peripheral surface of said braid;
  fitting at least one tubular polymeric section onto said polymeric adhesive layer; and
  cross-linking said at least one tubular polymeric section with the polymeric adhesive layer.

According to a preferred embodiment, the tubular polymeric section(s) can be cross-linked by heating, though other suitable means, such as an ultraviolet cure or using activated solvents can be used.

An advantage of the present invention is that endoscopic insertion tubes utilizing the above design can be more easily and cheaply manufactured than other known tubes.

Another advantage of the present invention is that providing a clear outer layer protects and increases the service life of printing which can now be disposed on an opaque interior layer.

Yet another advantage of the present invention is that providing a co-extruded sheath member having at least two layers allows different materials, including non-biocompatible material to be selectively incorporated intermediately within the sheath. This also allows more lubricious materials to be selected at the exterior of the tube without sacrificing flexibility.

Yet another advantage of the present invention is that the polymeric adhesive layer provides proper bonding of the braid to the sheath. Moreover, because the adhesive layer is made from a polymeric material, the shrinking of the sheath onto the tube assembly also allows permanent cross-linking.

Yet another advantage of the present invention is that an end collar of a particular design can be used with the described insertion tube to provide a smooth transition between the insertion tube and the bending portion thereof.

These and other objects, features, and advantages will now be described in accordance with the Detailed Description of the Invention which should be read in conjunction with the following drawings.

BRIEF DESCRIPTION OF THE DRAWINGS

FIG. 1 is a perspective partially cut-away view of an endoscope having an endoscopic insertion tube made in accordance with a first embodiment of the present invention;

FIG. 2 is a partial sectional view of the endoscopic insertion tube of FIG. 1;

DETAILED DESCRIPTION OF THE INVENTION

Figure 3:
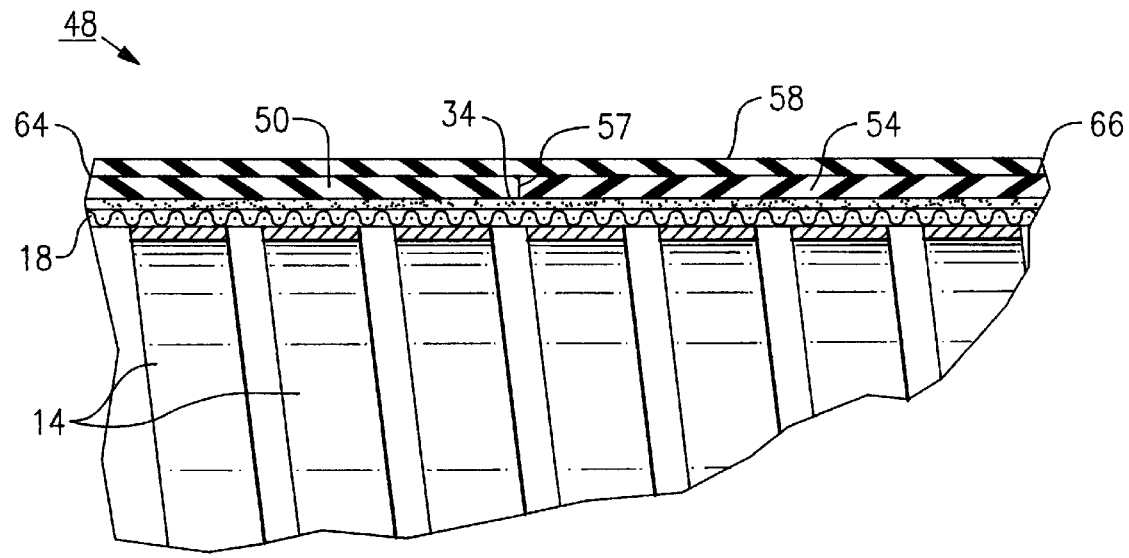
FIG. 3 is a partial sectional view of an endoscopic insertion tube made in accordance with a second embodiment of the present invention.

Referring to FIGS. 1 and 2, an endoscopic insertion tube 10 will now be described in accordance with a first embodiment of the present invention. The insertion tube 10 includes a flexible spiral tube 14 (also herein referred to as a monocoil) made from a thin section of stainless steel that is helically wound into a cylindrical tubular cross section. According to the present embodiment, the spiral tube 14 is made from a stainless steel, though other structural materials can easily be substituted.

A net-like braid 18, formed of metallic or other fibers formed into a knitted or interwoven configuration, is placed in overlaying relation onto the entirety of the length of the spiral tube 14, the braid also preferably being made from a stainless steel or other suitable material to form a tube sub-assembly 20. According to the present embodiment, the braid 18 is soldered or otherwise fixedly attached to the spiral tube 14 at respective distal and proximal ends 24, 25 of the tube sub-assembly 20.

Collars 22, 26 are respectively attached to the distal and proximal ends 24, 25 of the tube sub-assembly 20. According to the present embodiment, each of the end collars 22, 26 are cylindrical members made from stainless steel and having an appropriately sized interior cavity 27, including an annular shoulder 29 against which the ends of the tube sub-assembly 20 are retained, preferably by soldering. The end collars 22, 26 are each attached after the tube sub-assembly 20 has been cut to length.

Referring to FIG. 2, a thin polymeric adhesive layer 34 is then applied to the porous outer peripheral surface 19 of the net-like braid 18 and to the exterior portion of each end collar 22, 26 through conventional means such as spraying, painting or brushing. According to the present embodiment, the adhesive used is a two-part low viscosity polyurethane dispersion, which can be applied at room temperature and allowed to cure, either by waiting a predetermined period of time at room temperature or by placing the tube sub-assembly 20 into an appropriately sized oven (not shown) and heating, depending on the bonding requirements of the adhesive used. Other suitable adhesives can be used.

Referring to FIGS. 1 and 2, a first hollow tubular member 40, not shown in FIG. 1, is then placed in overlaying fashion onto the entirety of the length of the tube sub-assembly 20, including the exterior of the end collars 22, 26. The tubular member 40 according to this embodiment is made from a urethane rubber material and can include a set of exterior range or other printed markings (not shown) which are applied, such as by painting or other known means. Preferably, the inner diameter of the first tubular member 40 is pre-expanded to allow easy fitting over the outer periphery of the tube sub-assembly 20. For reasons articulated below, the first tubular member 40 need not be manufactured from a biocompatible material.

In accordance with the present embodiment, the first tubular member 40 is shrunk onto the tube assembly 20 by the application of heat, applied by conventional means, such as using an appropriately sized oven (not shown) or a heating tool (not shown). Sufficient heat, in excess of the glass transition temperature of the adhesive and the tubular material is applied to cause shrinking of the inner tubular member 40 to its original dimensions onto the outer periphery of the tube sub-assembly 20 and further to cause cross-linking between the urethane inner tubular member 40 and the polymeric adhesive layer 34. Alternately, other means of providing a cross-link can be utilized, such as application of ultraviolet radiation or use of heat activatable solvents, among others.

A hollow second tubular member 46, also made of a high-polymer material, is then placed over the outer peripheral surface 44 of the assembled first tubular member 40. The second tubular member 46 is made from a clear medical grade material which is presented to the remainder of the tube sub-assembly 20 in a pre-expanded condition, allowing the inner diameter of the second tubular member to fit over the outer diameter of the first tubular member 40 as well as the external diameter of the end collars 22, 26. Sufficient heat is applied to shrink the second tubular member 46 onto the outer peripheral surface 44 of the first tubular member 40. The amount of heat applied is also in excess of the glass transition temperature of the constituent materials of the first and second tubular members 46, 40, causing cross-linking therebetween. Other convenient means of providing a cross-link, as noted above, can alternately be used.

In its assembled form, the clear outer tubular member 46 allows the printing (not shown) applied to the outer peripheral surface 44 of the first tubular member 40 to be protected, thereby increasing the life of the insertion tube 10.

A second embodiment of an insertion tube 48 made in accordance with the present invention is herein described with reference to FIGS. 1 and 3. For the sake of clarity, the same parts are labeled with the same reference numerals. According to this embodiment, a helical monocoil 14 and a net-like braid 18, each as previously described, are respectively attached to each other at respective distal and proximal ends. End collars 22, 26 are then attached to each end of the formed tube sub-assembly 20, each end collar being a cylindrical member having recesses 27 sized for receiving the ends thereof against an annular shoulder 29.

A light coating of a polymeric adhesive layer 34 is then brushed, painted or otherwise applied to the outer peripheral surface of the braid 18 and the exterior of the end collars 22, 26 and cured, also in the manner described above.

A first pair of hollow tubular urethane rubber members 50, 54 are then fitted over the outer periphery of the adhesive layer 34 in abutting and axial relation to each other. According to the present embodiment, each of the tubular sections 50, 54 are then cross-linked to the polymeric adhesive layer 34 and further to shrink the tubular sections 50, 54 onto the outer periphery of the tube sub-assembly 20. Preferably, each of the urethane rubber members 50, 54 have different hardnesses, to allow more or less compliance over various portions of the length of the insertion tube.

Sufficient heat is also locally applied to the abutting edges 57 of the tubular sections 50, 54 to fuse the tubular sections to each other, using a convenient heating tool (not shown). A second hollow tubular section 58 is then fitted onto the outer peripheral surfaces 64, 66 of each of the pair of assembled tubular sections 50, 54. Heat is then similarly applied, either using an oven, a heating tool, or other appropriate heating means, to shrink the outer tubular member 58 onto the outer peripheral surfaces of the abutting inner tubular members 50, 54 and to permanently cross-link the materials together.

As in the preceding description, the outer tubular member 58 is preferably made from a clear formulation of the urethane material to allow range markings to be applied to the outer periphery of the inner tubular members 50, 54.

Figure 4:
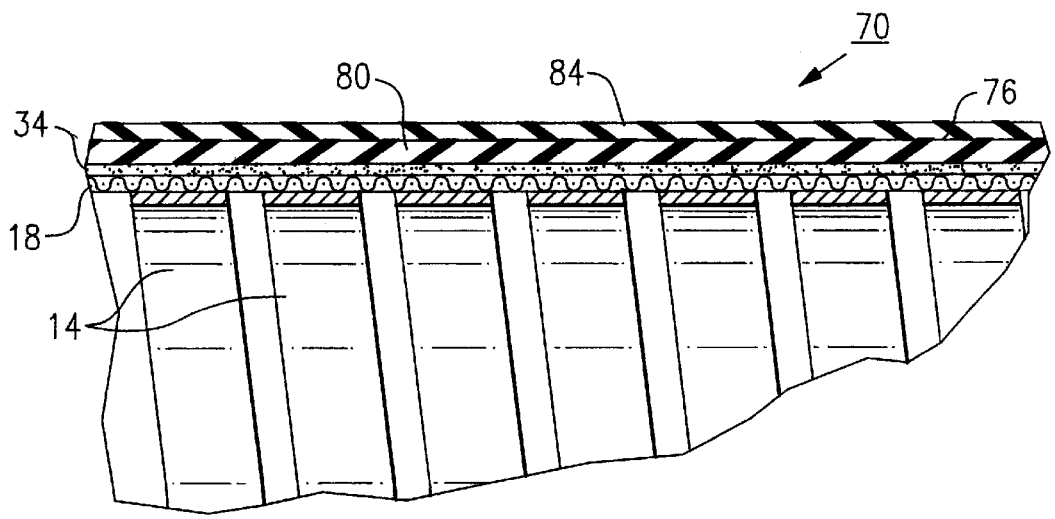
FIG. 4 is a partial sectional view of an endoscopic insertion tube made in accordance with a third embodiment.

A third embodiment of an insertion tube 70 is herein described with reference to FIGS. 1 and 4. As in the preceding, similar parts are labeled with the same reference numerals. The insertion tube 70 according to this embodiment includes the metallic spiral tube 14 wound into a helical configuration and the net-like braid 18 disposed over the length of the formed tube sub-assembly 20 in overlaying fashion as described above and shown most clearly in FIG. 1, each end of the braid/monocoil assembly being assembled into receiving cavities 27 provided in distal and proximal end collars 22, 26, respectively. As in the preceding, the braid 18 is preferably made from a suitable metal and includes a plurality of interstices. A thin polymeric adhesive layer 34 is then applied to the outer peripheral surface 19 of the braid 18 and a portion of the outer peripheral surface of the end collars 22, 26. The polymeric adhesive layer 34 is applied by conventional means, such as painting or spraying onto the tube sub-assembly 20 and is preferably a polyurethane or similar polymeric material, which is then allowed to cure to insure bonding.

A tubular composite member 76 is then applied over the outer periphery of the tube sub-assembly 20, the composite member including inner and outer layers 80, 84 of a high polymeric material formed as a result of a co-extrusion process. According to the present embodiment, the inner layer 80 is formed from a first polymeric material and the second or outer layer 84 is formed by applying a second polymeric material in overlaying fashion in a tubular configuration. As a result of co-extrusion, the inner and outer layers 80, 84 are already permanently cross-linked to one another.

According to the present embodiment, the assembly is then placed in an oven (not shown) and sufficient heat is applied to cause the composite tubular member 76 to shrink onto the tube sub-assembly 20, the shrinking process also causing the inner layer 80 of the sheath member to be permanently cross-linked with the polymeric adhesive layer 34.

Figure 5:
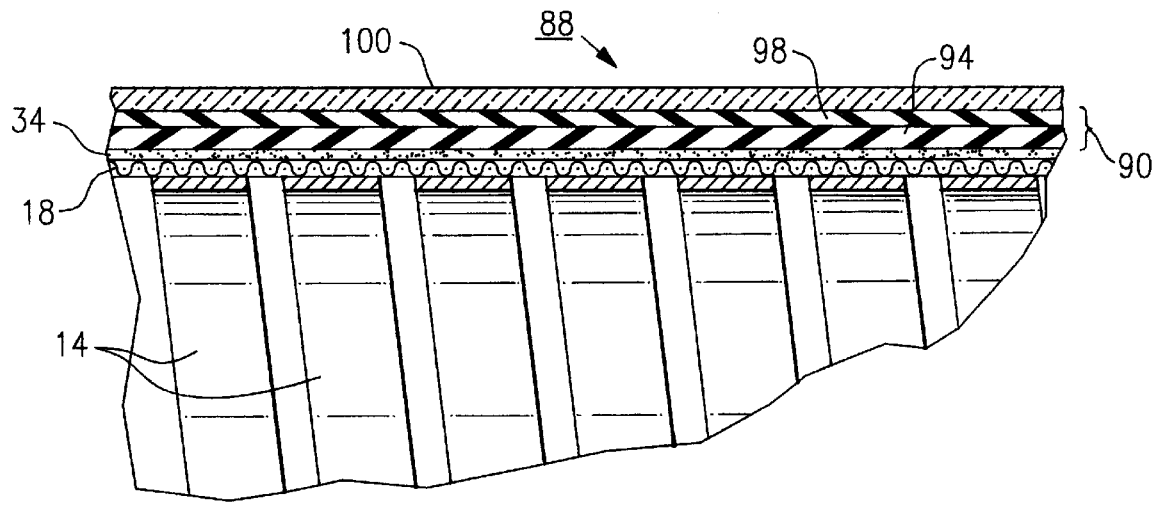
FIG. 5 is a partial sectional view of an endoscopic insertion tube made in accordance with a fourth embodiment of the present invention.

An insertion tube 88 in accordance with a fourth embodiment of the present invention is herein described with reference to FIGS. 1 and 5. As in the preceding, similar parts are labeled with the same reference numerals. The insertion tube 88 according to this embodiment also includes the spiral tube 14 and net-like braid 18 that covers the spiral tube. End collars 22, 26 are attached to distal and proximal ends 24, 25 of the tube sub-assembly 20 respectively, each having a recess or cavity 27 appropriately sized for receiving ends of the braid/monocoil portion of the sub-assembly. Finally, a polymeric adhesive layer 34 is then applied to the outer periphery 19 of the tube sub-assembly 20, in the manner previously described.

A composite hollow tubular member 90 is then fitted in a pre-expanded condition over the outer periphery of the tube sub-assembly 20. The composite tubular member 90 consists of inner and outer layers 94, 98 made from a high-polymer material. The composite tubular member 90 is formed using a co-extrusion process which permanently cross-links the inner and outer layers 94, 98 into an integral structure.

Heat or other suitable means is used to bond the composite member 90 to the tube sub-assembly 20, and to cause the inner layer 94 to permanently cross-link with the polymeric adhesive layer 34 and to allow the tubular composite member to be shrunk onto the tube sub-assembly 20.

According to this embodiment, an additional tubular member 100 can be fitted over the outer periphery of the composite member 90, the member being made from a clear formulation of a high polymer material which is suitably biocompatible for endoscopic applications. According to this embodiment, the tubular member 100 is hollow and is sized to allow the member to be fitted over the outer periphery of the composite member 90. The tubular member 100 is then cross-linked with the composite member 90, thereby protecting printing (not shown) applied to the outer periphery of the composite member, such as in the manner previously described.

Figure 6:
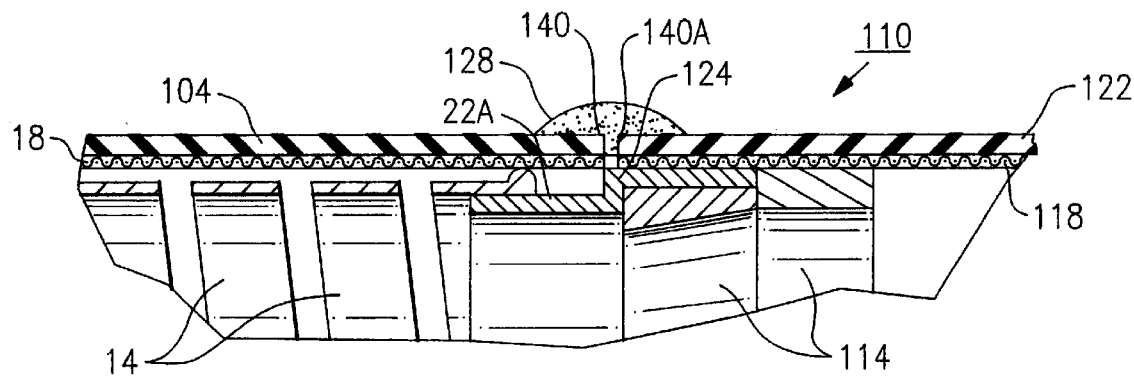
FIG. 6 is a partial sectional view of a distal end of an endoscopic tube in accordance with the prior art.
Figure 7:
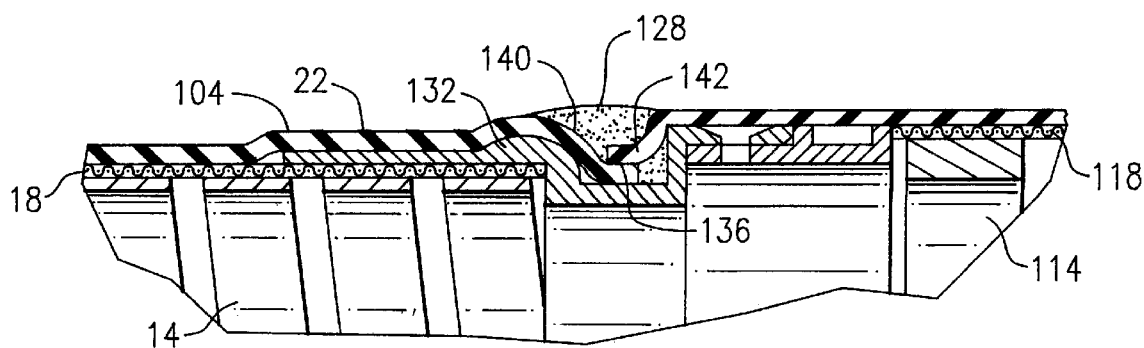
FIG. 7 is a partial sectional view of the proximal end of the endoscopic tube of FIGS. 1–5, in accordance with a preferred embodiment of the present invention.

Referring to FIG. 6 and 7, the exterior of the distal end collar 22 allows a smoother transition when bonding the above described insertion tube to a bending portion 110. As a matter of background, the bending portion 110, shown partially, is a tubular section which is similarly constructed; that is, having an underlying helical monocoil 114, braid 118 which forms a sub-assembly, and a tubular sheath 122 which covers the sub-assembly. Details regarding the bending portion 110 are commonly known in the field and require no further discussion herein, except where indicated.

In the assembly of a finished endoscopic tube, it is required to bond respective ends of the insertion tube and the bending portion 110 together onto the distal end collar 22. The monocoil/braid end portions of each respective tube subassembly are retained within cavities 27A, 130 of the distal collar, with the urethane covering portions 104,122 being epoxied together on the exterior thereof.

Previously, and referring to FIG. 6, known distal collars 22A have included a stepped interface region 124, causing the formation of a pronounced bead of epoxy 128 to protrude from the completed tube assembly after the ends 140A, 142A of the insertion tube and the bending portion 110 have been arranged in abutting relation on the distal end collar 22A.

Referring to FIG. 7, the present distal end collar 22 includes a rounded exterior portion 132 and a grooved interface area 136, in which the groove is sized to allow the ends 140, 142 of each of the tubular urethane covering sections 104, 122, to be fitted one on top of the other, and allowing the bead of epoxy 128 to fill the grooved interface area and provide a very uniform transition between the adjacent sections. In passing, and for purposes of clarity, the urethane covering section 104 is represented as a single layer, though this section may include several layers, as described previously above.

Though the present invention has been described in terms of preferred embodiments, it should be readily apparent to those of sufficient skill in the field that variations and modifications are possible within the spirit and scope of the appended claims.

PARTS LIST FOR FIGS. 1–7

| | |
|---|---|
| 10 | insertion tube |
| 14 | spiral tube |
| 18 | net-like braid |
| 19 | outer peripheral surface-braid |
| 20 | tube sub-assembly |
| 22 | distal end collar |
| 22A | distal end collar |
| 24 | distal end |
| 25 | proximal end |
| 26 | proximal end collar |
| 27 | cavity |
| 29 | annular shoulder |
| 34 | polymeric adhesive layer |
| 40 | first tubular layer |
| 46 | second tubular layer |
| 48 | insertion tube |
| 50 | tubular section |
| 54 | tubular section |
| 58 | second tubular member |
| 64 | outer peripheral surface |
| 66 | outer peripheral surface |
| 70 | insertion tube |
| 76 | composite tubular member |
| 80 | inner layer |
| 84 | outer layer |
| 88 | insertion tube |
| 90 | composite tubular member |
| 94 | inner layer |
| 98 | outer layer |
| 100 | outer clear tubular member |
| 104 | sheath |
| 110 | bending section |
| 114 | helical monocoil |
| 118 | braid |
| 122 | tubular sheath |
| 124 | stepped interface area |
| 128 | epoxy bead |
| 130 | cavity |
| 132 | rounded exterior portion |
| 136 | recessed interface area |
| 140 | end |
| 140A | end |
| 142 | end |
| 142A | end |

I claim:

1. An endoscopic insertion tube comprising:

a helically wound spiral tube;

a net-like braid placed over the length of said helically wound spiral tube in overlaying relation;

a polymeric adhesive layer coating the outer periphery of said braid; and a sheath covering said polymeric adhesive layer, said sheath comprising a multi layer structure including at least two layers, an inner layer fitted over the polymeric adhesive layer and an outer layer disposed over the outer periphery of said inner layer, wherein said inner layer and said outer layer are made from a high-polymer material and in which the inner layer of said sheath is cross-linked to said polymeric adhesive layer.

2. An endoscopic insertion tube as recited in claim 1, wherein said sheath comprises at least two layers formed into a unitary member using a co-extrusion process.

3. An endoscopic insertion tube as recited in claim 2, wherein said unitary member includes at least two layers, each said layer having a different hardness.

4. An endoscopic insertion tube as recited in claim 2, wherein said unitary member includes at least one inner layer and an outer layer, in which said at least one inner layer is made from a material chosen from a group consisting of either a biocompatible or non-biocompatible material, while said outer layer is made from a material which is biocompatible.

5. An endoscopic insertion tube as recited in claim 2, wherein said unitary member includes at least one inner layer and an outer layer, in which said outer layer is made from a material which allows said layer to be more lubricious than said at least one inner layer.

6. An endoscopic insertion tube as recited in claim 1, wherein said inner layer comprises at least two tubular sections, each of said tubular sections being cross-linked to said polymeric adhesive layer and disposed in axial relation wherein each of said tubular sections are made from a non-polymer material having a different hardness for controlling flexibility of said insertion tube.

7. An endoscopic insertion tube as recited in claim 6, wherein abutting edges of said at least two tubular sections of said inner layer are fused together.

8. An endoscopic insertion tube as recited in claim 1, wherein said inner layer of said sheath comprises an opaque high-polymer material including an outer peripheral surface having printing affixed thereto, said outer layer comprising a clear high-polymer material for covering and protecting the affixed printing of said inner layer.

9. An endoscopic insertion tube as recited in claim 8, wherein said inner and outer layers are made from a urethane rubber.

10. An endoscopic insertion tube as recited in claim 8, wherein said outer layer is made from a biocompatible material.

11. An endoscopic insertion tube as recited in claim 10, wherein said inner layer is made from a non-biocompatible material.

12. An endoscopic insertion tube as recited in claim 1, including an end collar attached at respective ends of said tube, each of said collars having a cavity sized for receiving ends of said braid and said helically wound spiral tube.

13. An endoscopic insertion tube as recited in claim 12, wherein said adhesive polymeric layer is applied to at least a portion of an outer peripheral surface of each of said end collars.

14. An endoscopic insertion tube as recited in claim 13, wherein said inner layer of said sheath is placed over the portion of each end collars having applied adhesive layer, wherein said inner layer is cross-linked to the adhesive layer.

15. An endoscopic tube as recited in claim 14, including a distal end and a proximal end in which the end collar attached to the proximal end of said tube includes a transition portion on said outer peripheral surface allowing an instrument portion to be attached thereto.

16. A method for manufacturing a flexible endoscopic insertion tube, said method comprising the steps of:

placing a net-like braid over the length of a helical metal inner coil member in overlaying fashion;

applying a polymeric adhesive layer onto the outer peripheral surface of said braid;

fitting at least one tubular polymeric section onto said polymeric adhesive layer; and cross-linking said at least one tubular polymeric section with said polymeric adhesive layer.

17. A method as recited in claim 16, wherein said cross-linking step includes the step of heating said at least one tubular polymeric section until cross-linking of said section with said adhesive layer occurs.

18. A method as recited in claim 16, wherein said cross-linking step includes the step of applying radiation to said at least one tubular section to effect cross-linking with said adhesive layer.

19. A method as recited in claim 16, wherein said cross-linking step includes the step of utilizing a heat activated solvent between said adhesive layer and tubular section to effect cross-linking therebetween.

20. A method as recited in claim 16, including the step of co-extruding a tubular polymeric section made from at least two layers of a high-polymer material, said at least two layers being cross-linked together prior to said fitting step.

21. A method as recited in claim 20, including the step of co-extruding said tubular polymeric section using at least two layers which are made from materials having different hardnesses.

22. A method as recited in claim 16, including the additional steps of:

fitting a first polymeric tubular section onto said polymeric adhesive layer;

cross-linking said first polymeric tubular section with the polymeric adhesive layer;

fitting a second polymeric tubular section onto the outer peripheral surface of said first polymeric tubular section; and cross-linking said second polymeric tubular section with said first polymeric tubular section.

23. A method as recited in claim 22, wherein said first polymeric section includes at least two tubular members made from high-polymer materials of different hardness, wherein said first fitting step includes fitting each of said tubular members in abutting axial relation onto said polymeric adhesive layer.

24. A method as recited in claim 22, including the step of applying printing to the outer peripheral surface of said first polymeric tubular section, wherein said second polymeric tubular section is made from a clear material.

25. A method as recited in claim 22, including the step of coextruding said second polymeric section from at least two layers.

26. A method as recited in claim 25, including the step of making each of said at least two layers of second tubular section from clear polymeric materials.

27. A method as recited in claim 16, including the step of attaching end collars to respective ends of said insertion tube, each of said end collars including a cavity sized for receiving ends of said braid and helical tube.

* * * * *